United States Patent [19]

Eremeev et al.

[11] Patent Number: 4,481,218

[45] Date of Patent: Nov. 6, 1984

[54] 3-(2,2,2-TRIMETHYLHYDRAZINIUM)PROPIONATE AND METHOD FOR THE PREPARATION AND USE THEREOF

[75] Inventors: Anatoly Eremeev, Riga; Ivars Y. Kalvinsh, Salaspils; Valentina G. Semenikhina; Edvards E. Liepinsh, both of Riga; Yan Y. Latvietis; Paul P. Anderson, both of Elgava; Elena B. Astapenok; Yazep Y. Spruzh, both of Riga; Petr T. Trapentsiers, Elgava; Gennady I. Podoprigora, Moscow, all of U.S.S.R.; Solomon A. Giller, deceased, late of Riga, U.S.S.R., by Ida I. Khiller, administratrix.

[73] Assignee: Institut Organicheskogo Sinteza Akademii Nauk Latviiskoi SSR, U.S.S.R.

[21] Appl. No.: 396,490

[22] Filed: Jul. 8, 1982

Related U.S. Application Data

[63] Continuation of Ser. No. 194,295, filed as PCT SU 79/00060, Jul. 27, 1979, published as WO 80/01068, May 29, 1980, § 102(e) date Jul. 25, 1980.

[30] Foreign Application Priority Data

Nov. 27, 1978 [SU] U.S.S.R. ................................ 2715660

[51] Int. Cl.$^3$ .................... C07D 29/12; C01B 25/16; E05B 63/14
[52] U.S. Cl. ............................... 424/316; 260/501.13; 71/113
[58] Field of Search ................... 260/501.13; 424/316; 71/113

[56] References Cited

FOREIGN PATENT DOCUMENTS 2546051 5/1976 Fed. Rep. of Germany .
2344232 10/1977 France .
1476615 6/1977 United Kingdom .
1495305 12/1977 United Kingdom .

OTHER PUBLICATIONS

Strova et al, Chemical Abstracts, vol. 66, 765(m), 1967.
Utsahomiya et al, Chemical Abstracts, vol. 68, 69306(a), 1968.
Wagner & Zook, Synthetic Organic Chemistry, John Wiley & Sons Inc., N.Y. pp. 416 and 417, (1965).
Zapevalova et al, Chemical Abstracts, vol. 66, No. 85394(s), 1967.
Hillers et al, Chemical Abstracts, vol. 85, No. 20962(y), 1976.
Inukgi et al, Chemical Abstracts, vol. 64, No. 584(h), 1966.
Semin et al, Chemical Abstracts, vol. 78, No. 3065(w), 1973.

*Primary Examiner*—Alton D. Rollins
*Assistant Examiner*—Raymond Covington
*Attorney, Agent, or Firm*—Steinberg & Raskin

[57] ABSTRACT

The novel compound according to the invention 3-(2,2,2-trimethylhydrazinium)-propionate has the general formula:

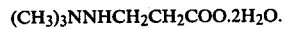

$(CH_3)_3NNHCH_2CH_2COO.2H_2O$.

The method for preparing this novel compound comprises passing a solution of 3-(2,2,2-grimethylhydrazinium) alkylpropionate of the formula:

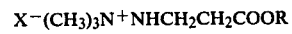

$X^-(CH_3)_3N^+NHCH_2CH_2COOR$ wherein X is Cl, Br, I, CH$_3$SO$_4$, R is a loawer alkyl, through a column with a strongly-basic anion exchange resin, followed by isolation of the desired product. The growth stimulator for animals and fowl contains the novel compound, i.e. 3-(2,2,2-trimethylhydrazinium)-propionate as the active principle.

6 Claims, No Drawings

3-(2,2,2-TRIMETHYLHYDRAZINIUM)PROPIONATE AND METHOD FOR THE PREPARATION AND USE THEREOF

This is a continuation of application Ser. No. 194,295 filed July 27, 1980.

FIELD OF THE INVENTION

The present invention relates to a novel compound out of the class of novel chemical compounds—linear hydrazinium betaines—3-(2,2,2-trimethylhydrazinium)-propionate, a method for preparing same and use as an active principle for a growth stimulator for fowl and animals.

BACKGROUND OF THE INVENTION

Compound having a betaine structure with a hydrazinium group as a positively charged grouping have not been hitherto described in the literature, The compound according to the present invention, viz. 3-(2,2,-trimethylhydrazinium)propionate possessing this structure is novel and hitherto unknown from the literature.

Known in the art is the use, as growth stimulator for farm animals and fowl, of antibiotics such as chlorotetracycline, nitrofuran preparations, arsenic derivatives, enzymes, hormones, tissue preparations, phosphatides and the like. However, antibiotics and nitrofuran preparations are efficient only under conditions of infection. On the other hand, substantially all of the known growth stimulators: antibiotics, enzymatic preparations, are economically inefficient. Some of these such as arsenic preparations, are toxic. In cases of the use of antibiotics it is necessary to take into consideration the real risk of origination of resistant, bacteria strains, such as pathogenic strains e.g. E.coli. Residual amounts of antibiotics in meat products and eggs can cause allergic diseases.

U.S. Pat. No. 2,925,342, published 02.16.60, Cl. nat. C I.99-2.

U.S. Pat. No. 3,017,272 published 01.16.62, Cl.nat. C I.99-2; U.S. Pat. No. 3,639,595 published 02.01.72, Cl.Int. A 61 k 21/00;

French Pat. No. 2,137,731 published 02.02.73, Cl.Int. A 23 k 1/00; FRG Pat. No. 1,692,477 published Oct. 19, 1972, Cl. 53 g 4/04).

SUMMARY OF THE INVENTION

According to the present invention, the novel chemical compound 3-(2,2,2-trimethylhydrazinium)-propionate has the following formula:

$$(CH_3)_3N^+NHCH_2CH_2COO^- \cdot 2H_2O \qquad (1)$$

The method for preparing said compound 3-(2,2,2-trimethylhydrazinium)-propionate comprises passing a solution of 3-(2,2,2-trimethylhydrazinium)alkylpropionate of the formula:

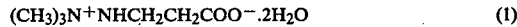

$$X^-(CH_3)_3N^+NHCH_2CH_2COOR$$

wherein X is Cl, Br, I, $CH_3SO_4$, R is a lower alkyl through a column with a strongly basic anion exchange resin, followed by isolation of the desired product.

It is advisable to use a solution of 3-(2,2,2-trimethylhydrazinium)alkylpropionate in water or in a polar organic solvent.

As the polar organic solvent use is preferably made of methanol or ethanol. According to the present invention, the growth stimulator involving an active principle and a vehicle contains, as the active principle, 3-(2,2-trimethylhydrazinium-propionate. It is preferred to use the growth stimulator for animals and fowl with a content of the active principle of from 0.001 to 0.5% by weight.

DETAILED DESCRIPTION OF PREFERRED EMBODIMENTS

The compound according to the present invention, viz. 3-(2,2,2-trimethylhydrazinium)propionate comprises a colourless crystalline powder with a melting point of 254°–256° C. (from ethanol). It is very readily soluble in water, well soluble in ethanol and methanol. The PMR in deuterized water reveals the presence of the following signals $\tau$ (p.p.m.): 6.70 singlet, $(CH_3)_3N$; 6.89, triplet, $CH_2$, The toxicological study of 3-(2,2,2-trimethylhydrazinium)-propionate on white mice weighing 20–25 g has shown that with a single peroral administration to the animals in doses of up to 23,000 mg/kg the preparation causes no death of the animals. When administered intraperitoneally, doses of up to 10,000 mg/kg of 3-(2,2,2-trimethylhydrazinium)propionate proved to be non-toxic, No pathological changes in vitally important organs are observed upon administration of the preparation to white rats weighing 200–250 g perorally in doses of 100 mg/kg every day within the period of 3 months.

The study of specific activity of 3-(2,2,2-trimethylhydrazinium)-propionate was effected on various animals: mice, rats, pigs, cattle, chickens, goslings, turkey poults and ducklings. The growth-controlling activity of this compound relative to plats has been studied on barley, oats, rye and wheat.

It has been found that 3-(2,2,2-trimethylhydrazinium)-propionate possesses a clearly pronounced growth-stimulating activity relative to animals and fowl. Depending on the variety of animals and fowl, the compound according to the present invention ensures a daily weight gain of 8–24%. At the same time, in the test animals and fowl, metabolism is improved and the rate of feedstock consumption is reduced by 7–15% per weight gain unit.

In the investigation of the activity of 3-(2,2,2-trimethylhydrazinium)-propionate on plants it has been found that this compound possesses a clearly pronounced growth-controlling effect. This compound ensures a 15% increase in the stem diameter of crops such as oats, barley, rye, wheat, thus improving their stability against lodging.

Furthermore, specific gravity of grain crops is increased, thus causing, in general, a yield gain of these crops by 15–30%.

3-(2,2,2-Trimethylhydrazinium)-propionate comprises the active principle of a growth-stimulator for animals and fowl. This compound can be used with any vehicle suitable for feeding to animals and fowl, such as water, milk, as well as in a mixture with a feedstuff or any other suitable filler. The growth stimulator for animals and fowl is administered daily in a single dose or several times per day. The efficiency of the growth stimulant does not substantially depend on the mode and number of administrations and is defined mainly by the dose and duration of feeding. The growth stimulant is employed for different kinds of animals and fowl and a preferred content of the active principle is varied within the range of from 0.001 to 0.5% by weight, or 0.1–100 mg per kg of the animal body weight.

The compound according to the present invention, viz. 3-(2,2,2-trimethylhydrazinium)-propionate is produced by passing a solution of a 3-(2,2,2-trimethylhydrazinium)-alkylpropionate of the general formula:

wherein X is Cl, Br, I, $CH_3SO_4$, R is a lower alkyl, through a column with a strongly-basic anion exchange resin, followed by isolation of the desired product. The nature of the anion does not affect the yield and quality of the desired product. Use is made mainly of salts of 3-(2,2,2-trimethylhydrazinium)alkylpropionates, wherein the alkyl radical is methyl, ethyl, propyl or other lower alkyl radicals. The specific feature of the method according to the present invention for the preparation of 3-(2,2,2-trimethylhydrazinium)-propionate resides in that passing a solution of a salt of 3-(2,2,2-trimethylhydrazinium)-alkylpropionate through a column with a strongly-basic anion exchange resin such as Amberlite IRA-400 or another strongly-basic resin causes hydrolysis of the estereal grouping simultaneously with exchange of the acid anion to hydroxy ion, thus considerably reducing the synthesis duration. In the process according to the present invention use can be made of any suitable solvent such as water, a polar organic solvent (alcohols and the like) so that the solvent nature does not substantially affect the yield and purity of the desired product.

For a better understanding of the present invention some specific examples illustrating the method for preparing the novel compound 3-(2,2,2-trimethylhydrazinium)-propionate and use are given hereinbelow.

EXAMPLE 1

A solution of 196.5 g (1 mole) of 3-(2,2,2-trimethylhydrazinium)-methylpropionate chloride in 500 ml of water is passed through a column with the ion-exchange resin Amberlite IRA-400. The solvent is evaporated, the residue is crystallized from ethanol. The yield of 3-(2,2,2-trimethylhydrazinium)-propionate is 140 g (85%); the product comprises colourless crystals melting at 254°–256° C. The PMR-spectrum ($\tau$, p.p.m.): 6.70, singlet, $(CH_3)_3N^+$; 6.89, triplet, $CH_2$; 7.77, triplet, $CH_2$. Found, %: C 39.56; H 10.10; N 15.36; $C_6H_{14}O_2N_2.2H_2O$. Calculated, % C 39.56; H 9.89; N 15.30.

EXAMPLE 2

A solution of 272 g (1 mol) of 3-(2,2,2-trimethylhydrazinium)-methylpropionate methylsulphate in 500 ml of methanol is passed through a column filled with an ion-exchange resin. The solvent is evaporated, the residue is crystallized from ethanol. The yield of the desired product is 148 g (90%) in the form of colourless crystals. The product characteristics are similar to those described in the foregoing Example 1.

EXAMPLE 3

A solution of 210.5 g (1 mol) of 3-(2,2,2-trimethylhydrazinium)-ethylpropionate chloride in 800 ml of ethanol is passed through a column with an ion-exchange resin (Amberlite IRA-400) and the solvent is evaporated. There are obtained 146 g (about 88%) of 3-(2,2,2-trimethylhydrazinium)-propionate as colourless crystals. The product characteristics are similar to those described in Example 1.

EXAMPLE 4

A solution of 244.9 g (1 mol) of 3-(2,2,2-trimethylhydrazinium)-ethylpropionate bromide in 500 ml of water is passed through a column with the ion-exchange resin Amberlite IRA-400, then the solvent is evaporated to give 147 g (about 87%) of 3-(2,2,2-trimethylhydrazinium)-propionate as colourless crystals. The product characteristics are similar to those of Example 1 hereinabove.

EXAMPLE 5

A solution of 277 g (1 mol) of 3-(2,2,2-trimethylhydrazinium)-methylpropionate iodide in 500 ml of water is passed through a column with the ion-exchange resin Amberlite IRA-400, whereafter the solvent is evaporated to give 140 g (85%) of 3-(2,2,2-trimethylhydrazinium)-propionate as colourless crystals. The product characteristics are similar to those described in Example 1.

EXAMPLE 6

The growth stimulator for animals and fowl containing 3-(2,2,2-trimethylhydrazinium)-propionate as the active principle is tested for efficiency. The test is conducted in chicks of 6 days of age, the test group consisting of 50 chicks and the control group—50 chicks. The test chicks were fed with a feedstuff containing 0.02% by weight of the active principle, the control group—only basic diet without the addition of the active principle. The chicks' diet contained, % by weight: barley—20, wheat—6, corn—40, sunflower and soyabean grist—19, fish flour—7, meat-bone flour—3, yeast—5. One kilogram of the feedstuff contained 1.25 feeding unit, 3,135 kCal of exchange energy, 21% of a crude protein, 4% of crude cellulose and 197 g of digestable protein. The experiment was carried out for 34 days and by its end the chicks' weight was 440.5 g on the average in the test group vs. 412.2 g of the average weight of the control group chicks, i.e. the chicks fed with 0.02% by weight of the feedstuff of the additive 3-(2,2,2-trimethylhydrazinium)-propionate had a weight gain of 7.7% compared to the control chicks. The test results are shown in Table 1.

TABLE 1

| No. | Feedstuff characteristic | Average body weight of chicks, g, aged: | | | Average gain for the test time | Percentage to the control |
|---|---|---|---|---|---|---|
| | | 6 days | 30 days | 40 days | | |
| 1. | Without special additives (control) | 42.7 | 274.0 | 412.2 | 364.5 ± 10.1 | 100.0 |
| 2. | With the addition of 0.02% by weight of 3-(2,2 2-trimethylhydrazinium)-propionate | 47.8 | 289.4 | 440.5 | 392.7 ± 9.9 | 107.7 |

EXAMPLE 7

The experiment for testing efficiency of the growth stimulant for animals and fowl according to the present invention was carried out following the procedure similar to that described in the foregoing Example 6; added to the feedstuff was 0.04% by weight of the active principle based on the feedstuff weight. By the end of the 34-days' period the chicks of the test groups fed with the growth stimulant were 12.9% heavier. The test results are shown in the following Table 2.

TABLE 2

| No. | Feedstuff characteristic | Average body weight of chicks, g. aged: 6 days | Average body weight of chicks, g. aged: 30 days | Average body weight of chicks, g. aged: 40 days | Average mass gain for the test time, g | Percentage to the control |
|---|---|---|---|---|---|---|
| 1. | Without additive (control) | 54.0 | 261.9 | 364.3 | 313 ± 3 | 100.0 |
| 2. | With the addition of 0.04% by weight of 3-(2,2,2-trimethylhydrazinium)-propionate | 51.0 | 268.9 | 404.8 | 353 ± 8 | 112.9 |

EXAMPLE 8

The efficiency of the growth stimulant for animals according to the present invention was tested in feeding of microbless animals. The test was carried out in microbless pig mini-sucklings grown without under sterile conditions in a comparison with pig mini sucklings grown keeping to the requirements of sterile conditions, since birth and to the age of two-months, a feedstuff containing 0.04% by weight of the active principle. Their growth was compared to that of 10 sucklings grown without keeping to sterility conditions and the development of 7 microbless pig sucklings. By the end of the experiment the test pig sucklings were 17.2% heavier than the microbless pig sucklings given no growth stimulant and 18.2% heavier than the sucklings grown under nonsterile conditions and given no growth stimulator. The test results are shown in the following Table 3.

TABLE 3

| No. | Animal category | Animal weight at the 2-months' age, g | Number of animals in the group |
|---|---|---|---|
| 1. | Ordinary pig sucklings given no growth stimulator | 3,244 ± 335 | 10 |
| 2. | Microbless mini-pigs (sucklings) given no growth stimulant | 3,271 ± 385 | 7 |
| 3. | Microbless mini-pigs fed with the growth stimulator in the amount of 0.04% by weight of the active principle (based on the feedstuff) | 3,833 ± 348 | 5 |

EXAMPLE 9

The efficiency of the growth stimulator was tested on white-breed young pigs deprived of mother's milk with the body weight of about 20 kg, 10 kgs, in each group.

The young pigs were in the same pig sty and serviced by one operator; all of the animals were on the same diet consisting of barley flour, green mass of a vetch-oat mixture and whey. The animals were fed two times a day with free watering. To the feedstuff of the test group there were added 200 mg of 3-(2,2,2-trimethylhydrazinium)propionate per 1 kg of dry substance of the feed-stuff (0.02% by weight of the active principle). It was found that the pigs given the growth stimulator for 122 days had a weight gain by 7.4 kg higher as compared to the control group animals, while the consumption of feeding units per every kilogram of the weight gain is by 7.1% less. The test results are shown in Table 4.

TABLE 4

| Characteristic | Group of animals Test | Group of animals Control |
|---|---|---|
| Number of animals | 10 | 10 |
| Average body weight by the test beginning, kg | 21.8 ± 1.5 | 20.0 ± 1.67 |
| Average body weight by the test end, kg | 88.2 ± 4.0 | 74.0 ± 3.2 |
| Body weight gain during the test period, kg | 66.4 ± 3.6 | 59.0 ± 2.1 |
| Average daily weight gain, kg | 544 ± 32 | 484 ± 17 |
| Average daily weight gain, percent of the control | 112.4 | 100.0 |
| Feedstuff consumption during the test period, feeding units | 270.7 | 285.5 |
| Feedstuff consumption per 1 kg of the body weight gain, feeding units | 4.07 | 4.38 |
| Feedstuff consumption per 1 kg of the body weight gain % of control | 92.9 | 100.0 |

EXAMPLE 10

The efficiency of the growth stimulator was studied on young rats. The experiment was carried out with nondescript young rats weighting about 75 g in groups of 30 animals in each. The growth stimulator was administered perorally to each rat as an aqueous solution at a rate of from 0.1 to 0.001% by weight of the consumed daily diet. The administration of the growth stimulator was effected every day during 10 days. The observation period was 20 days; the rats were weighed after every 4 days. It was found that 3-(2,2,2-trimethylhydrazinium)-propionate in the dose of 0.1% by weight of the consumed daily diet substantially did not affect the weight gain of the rats, whereas the addition of 0.01% and 0.001% by weight of the consumed daily diet increased the body weight gain of the rats by 12 and 12.5% respectively. On completion of the experiment the animals were killed and the parenchymatous organs and peripheral blood were analyzed. No pathology was observed. The test results are shown in Table 5.

TABLE 5

| No. | Animal category | Weight on the day of weighing, g since the beginning of feeding 4 | 8 | 12 | 16 | 20 |
|---|---|---|---|---|---|---|
| 1. | Animal given no growth stimulator | 74 ± 5 | 89 ± 7 | 101 ± 6 | 116 ± 9 | 131 ± 10 |
| 2. | Animals given the growth stimulator with 0.1% of the active principle | 76 ± 4 | 95 ± 6 | 98 ± 5 | 107 ± 8 | 129 ± 6 |
| 3. | Animals given the growth stimulator with 0.01% of the active principle | 79 ± 5 | 93 ± 8 | 125 ± 10 | 139 ± 7 | 158 ± 9 |
| 4. | Animals given the growth stimulator with the content | 76 ± 5 | 99 ± 7 | 131 ± 8 | 154 ± 8 | 164 ± 7 |

TABLE 5-continued

| No. | Animal category | Weight on the day of weighing, g since the beginning of feeding | | | | |
|---|---|---|---|---|---|---|
| | | 4 | 8 | 12 | 16 | 20 |
| | of the active priciple of 0.001% | | | | | |

EXAMPLE 11

The growth stimulator efficiency was studied on pubertal rats. The experiment conditions were similar to those described in the foregoing Example 10. It was found that the growth stimulator with the content of the active principle of 0.101% and 0.001% by weight of the dry feedstuff results in the body weight gain of the by 9 and 13.5% respectively. The test results are shown in the following Table 6.

TABLE 6

| No. Animal category | Weight, g, on the weighing day | | | | |
|---|---|---|---|---|---|
| | 4 | 8 | 12 | 16 | 20 |
| 1. Animals given no growth stimulator | 160 ± 11 | 168 ± 10 | 179 ± 12 | 188 ± 9 | 209 ± 13 |
| 2. Animals given the growth stimulant with 0.1% of the principle | 155 ± 10 | 161 ± 10 | 174 ± 8 | 187 ± 11 | 203 ± 9 |
| 3. Animals given the growth stimulator with 0.01% of the active principle | 169 ± 7 | 175 ± 8 | 189 ± 13 | 215 ± 12 | 229 ± 11 |
| 4. Animals given the growth stimulator with 0.001% of the active principle | 175 ± 11 | 189 ± 12 | 210 ± 9 | 231 ± 14 | 248 ± 12 |

INDUSTRIAL APPLICABILITY

The novel compound according to the present invention, i.e. 3-(2,2,2-trimethylhydrazinium)-propionate possesses the ability of controlling plant growth, stimulating growth of animals and fowl, wherefore it is useful in agriculture for increasing yield of crops and stimulation of growth of animals and fowl. The novel compound according to the present invention can be also useful as an intermediate product for the synthesis of polyamide resins.

We claim:

1. 3-(2,2,2-Trimethylhydrazinium)-propionate of the formula:

$$(CH_3)_3N^+NH\ CH_2CH_2COO^-.2H_2O \qquad (1)$$

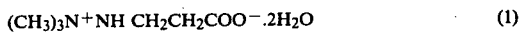

2. A growth stimulator for animals and fowl containing a growth stimulating effective amount of an active principle and a vehicle, characterized in that the active principle is 3-(2,2,2-trimethylhydrazinium)-propionate of claim 1.

3. A growth stimulator for animals and fowl according to claim 2, characterized in that the active principle is present in an amount of 0.001 to 0.5% by weight.

4. Method for stimulating the growth of animals and fowl, which comprises administering to the animals or fowl requiring growth stimulation a growth stimulating effective amount of the compound of claim 1.

5. Method according to claim 4, wherein said growth stimulating effective amount is 0.1–100 mg/kg of animal body weight.

6. Method according to claim 4, wherein said compound is administered in an amount of 0.001% to 0.01% by weight of consumed daily diet.

* * * * *